(12) United States Patent
Rao et al.

(10) Patent No.: US 8,461,334 B2
(45) Date of Patent: Jun. 11, 2013

(54) PROCESS FOR RESOLVING ZOPICLONE

(75) Inventors: Dharmaraj Ramachandra Rao, Maharashtra (IN); Rajendra Narayanrao Kankan, Maharashtra (IN); Maruti Ganpati Ghagare, Maharashtra (IN); Sunilkumar Parasnath Saroj, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 13/127,944

(22) PCT Filed: Nov. 6, 2009

(86) PCT No.: PCT/GB2009/002628
§ 371 (c)(1),
(2), (4) Date: Jun. 8, 2011

(87) PCT Pub. No.: WO2010/052475
PCT Pub. Date: May 14, 2010

(65) Prior Publication Data
US 2011/0245499 A1     Oct. 6, 2011

(30) Foreign Application Priority Data
Nov. 7, 2008  (IN) .................. 2369/MUM/2008

(51) Int. Cl.
*C07D 487/04* (2006.01)
(52) U.S. Cl.
USPC ........................................ 544/350
(58) Field of Classification Search
USPC ........................................ 544/350
See application file for complete search history.

(56) References Cited

U.S. PATENT DOCUMENTS

| 6,339,086 | B1 | 1/2002 | Jerussi et al. |
| 6,444,673 | B1 | 9/2002 | Cotrel et al. |
| 2005/0043311 | A1* | 2/2005 | Cotrel et al. .................. 514/249 |
| 2007/0054914 | A1 | 3/2007 | Mandava et al. |
| 2008/0146800 | A1 | 6/2008 | Sawant et al. |
| 2008/0287447 | A1 | 11/2008 | Finkelstein et al. |

FOREIGN PATENT DOCUMENTS

| WO | 2007083188 A2 | 7/2007 |
| WO | 2007088073 A1 | 8/2007 |
| WO | 2008126105 A2 | 10/2008 |
| WO | 2009063486 A2 | 5/2009 |
| WO | 2009101634 A2 | 8/2009 |
| WO | 2010052475 A1 | 5/2010 |

OTHER PUBLICATIONS

Tartaric Acid Derivatives, http://www.made-in-china.com/showroom/likai-chiral/product-detailCeVnOyWrnfRI/China-Tartaric-Acid-Derivatives.html, accessed Aug. 1, 2012.*
Foreign communication from the priority application—International Preliminary Report on Patentability, PCT/GB2009/002628, May 19, 2011, 12 pages.
Foreign communication from the priority application—International Search Report and Written Opinion—PCT/GB2009/002628, Jan. 28, 2010, 13 pages.

* cited by examiner

*Primary Examiner* — Wu-Cheng Winston Shen
*Assistant Examiner* — Karen Cheng
(74) *Attorney, Agent, or Firm* — Conley Rose, P.C.; Rodney B. Carroll

(57) ABSTRACT

The present invention provides a process for the preparation of the dextrorotatory isomer of zopiclone (eszopiclone). The present invention also provides eszopiclone di-p-anisolyl-L-tartrate and eszopiclone diacetyl-L-tartrate, which are useful as intermediates in a process for preparing eszopiclone.

10 Claims, No Drawings

PROCESS FOR RESOLVING ZOPICLONE

CROSS-REFERENCE TO RELATED APPLICATIONS

This application is a filing under 35 U.S.C. 371 of International Application No. PCT/GB2009/002628 filed Nov. 6, 2009, entitled "Process for Resolving Zopiclone," claiming priority of Indian Patent Application No. 2369/MUM/2008 filed Nov. 7, 2008, which applications are incorporated by reference herein in their entirety.

FIELD OF INVENTION

The present invention describes a process for the preparation of the dextrorotatory isomer of zopiclone (eszopiclone) and intermediates for use in the process.

BACKGROUND OF THE INVENTION

Eszopiclone, first disclosed in U.S. Pat. No. 6,444,673, is a short acting nonbenzodiazepine hypnotic agent used in the treatment of insomnia which is the S-isomer of the racemic product zopiclone. As compared to the R-enantiomer, the S-enantiomer is found to be less toxic, binds more specifically to the GABA receptor and shows higher activity. The drug has been marketed in United States by Sepracor under the name Lunesta. Chemically eszopiclone is (S)-(+)-6-(5-chloro-2-pyridinyl)-7-oxo-6,7-dihydro-5H-pyrrolo-[3,4b]-pyrazin-5-yl-4-methyl-piperazine-1-carboxylate (Formula I), and is represented by the following structure.

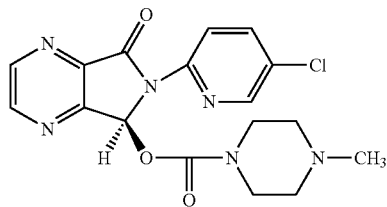

Formula I

U.S. Pat. No. 6,444,673 discloses the preparation of eszopiclone which involves resolving racemic zopiclone with O,O'-dibenzoyltartaric acid monohydrate to obtain the corresponding crude salt which is twice recrystallised with acetonitrile to obtain the pure salt (36 mol. % yield). The salt is further alkalinized and recrystallised again with acetonitrile solvent to yield 23 mol. % of eszopiclone.

The process disclosed above involves an excess of solvent in order to obtain pure eszopiclone. Also, the yield of the final product obtained by the process is low.

U.S. Pat. No. 6,339,086 discloses the preparation of eszopiclone using D-malic acid as a resolving agent and a mixture of methanol and acetone as a solvent. For the precipitation of the D-malate salt of eszopiclone, the process requires that the reaction mixture be heated in an oil bath and also seeding with the corresponding salt.

U.S. 2007/0054914 discloses the preparation of eszopiclone which involves resolving zopiclone with di-p-toluoyl-tartaric acid in the presence of an organic solvent. In U.S. 2007/0054914, the resolution step is carried out at room temperature. The problems associated with the process are that under the described conditions the selective crystallization of the desired enantiomer salt does not occur efficiently; hence it is difficult to isolate eszopiclone having a high chiral purity from the reaction mixture. The product has to be further purified at various stages to obtain the desired chiral and HPLC purity.

U.S. 2008/0287447, U.S. 2008/0146800, WO 2007083188, WO 2008126105, and WO 2009063486 disclose the resolution of eszopiclone from racemic zopiclone using various tartaric acid derivatives.

The preparation of eszopiclone described in the prior art processes involves multiple recrystallization in order to obtain an enantiomeric excess of eszopiclone. Further repetitive purifications decrease the yield of product. Also, the multiple recrystallizations cause an increase in the amount of solvent employed, thus making the process environmentally unfriendly and non-economical.

There is, therefore, a need for an improved or alternate process for the synthesis of eszopiclone having a high degree of chiral purity. The present invention is an attempt in providing a simple, economical, eco-friendly, industrially suitable and high yielding process for preparation of eszopiclone.

OBJECTS OF THE INVENTION

The object of the present invention is to provide an improved process for resolving eszopiclone.

Another object of the present invention is to provide a process that produces eszopiclone in high yield and enantiomeric purity.

SUMMARY OF THE INVENTION

According to a first aspect of the present invention, there is provided a process for preparing the di-p-anisolyl-L-tartrate or diacetyl L-tartrate salt of eszopiclone, which process comprises reacting racemic zopiclone with di-p-anisolyl-L-tartaric acid or diacetyl L-tartaric acid, respectively.

In an embodiment, the process is carried out in the presence of a solvent mixture. Preferably, the solvent mixture is a mixture of water and a polar aprotic solvent. Suitably, the polar aprotic solvent is selected from the group consisting of N,N-dimethylformamide, dimethylsulfoxide, N,N-dimethylacetamide, sulfolane, and N-methylpyrrolidone. Most preferably, the solvent mixture is a mixture of water and N-methylpyrrolidone.

Advantageously, the salt of eszopiclone has a chiral purity greater than or equal to 95%. As used throughout the specification, the term "chiral purity" means the purity as determined by chiral HPLC, and is calculated using the formula:

Chiral purity=100×[(R-isomer)/(R-isomer+S-isomer)]

where "R-isomer" in the above formula refers to the molar quantity of the R-isomer and "S-isomer" in the above formula refers to the molar quantity of the S-isomer.

According to another aspect of the present invention, there is provided a process for preparing a salt of eszopiclone, which process comprises reacting racemic zopiclone with a resolving agent in the presence of water and N-methylpyrrolidone. Suitably, the resolving agent is selected from the group consisting of diacetyl-L-tartaric acid, di-p-anisolyl-L-tartaric acid, di-p-toluoyl-L-tartaric acid, O,O'-dibenzoyl tartaric acid and tartaric acid. Preferably, the resolving agent is selected from the group consisting of diacetyl-L-tartaric acid and di-p-anisolyl-L-tartaric acid.

According to another aspect of the present invention, there is provided a process for preparing eszopiclone comprising preparing a salt of eszopiclone according to any preceding claim, and reacting the salt of eszopiclone with a base. Suitably, the base is selected from the group consisting of pyridine, dimethylamine, trimethylamine, sodium ethoxide, sodium carbonate, potassium carbonate, magnesium carbonate, calcium carbonate, sodium bicarbonate, and potassium bicarbonate.

In an embodiment, the eszopiclone is recrystallised using a solvent selected from ethanol, methanol, acetonitrile, acetone, ethyl acetate, or propanol. Preferably, the solvent is ethyl acetate. Advantageously, the eszopiclone has a chiral purity greater than or equal to 99%.

According to another aspect of the present invention, there is provided eszopiclone di-p-anisolyl-L-tartrate.

According to another aspect of the present invention, there is provided eszopiclone diacetyl-L-tartrate.

According to another aspect of the present invention, there is provided a process which comprises:
(a) preparing a salt of zopiclone according to any one of the processes described above;
(b) obtaining a mother liquor enriched in (R)-zopiclone;
(c) converting (R)-zopiclone obtained from step (b) to racemic zopiclone; and
(d) employing racemic zopiclone obtained from step (c) in a process according to any of one of the processes described above.

According to another aspect of the present invention, there is provided eszopiclone prepared according to any one of the processes described above.

According to another aspect of the present invention, there is provided a pharmaceutical composition comprising eszopiclone prepared according to any one of the processes described above together with one or more pharmaceutically acceptable excipients.

According to another aspect of the present invention, there is provided eszopiclone prepared according to any one of the processes described above for use in medicine, particularly for use in the treatment of insomnia.

According to another aspect of the present invention, there is provided a method of treating insomnia, the method comprising administering to a patient in need thereof a therapeutically effective amount of eszopiclone prepared according to any one of the processes described above.

DETAILED DESCRIPTION OF THE INVENTION

The invention will now be described in detail in connection with certain preferred and optional embodiments, so that various aspects thereof may be more fully understood and appreciated.

The process of the present invention relates to the resolution of zopiclone to provide the S-enantiomer of zopiclone (also called "eszopiclone") having a high optical purity.

In an embodiment, the present invention provides a process for the preparation of eszopiclone of Formula I, as shown in Scheme 1.

Scheme 1

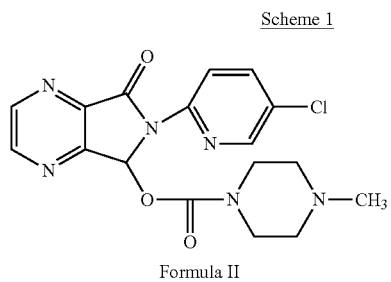

Formula II

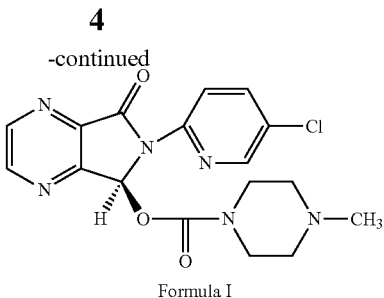

Formula I

Accordingly, the present invention relates to a process for preparing eszopiclone which process comprises:
a) resolving racemic zopiclone of Formula II with a resolving agent in the presence of a solvent mixture to obtain the corresponding salt of the resolving agent and eszopiclone; and
b) converting the salt prepared in step a) to eszopiclone.

Advantageously, the eszopiclone prepared according to the process of the present invention is substantially free of R-zopiclone.

In an embodiment, the resolving agent is a chiral tartaric acid derivative which may be selected from the D- and L-isomers of di-p-anisolyl-tartaric acid and diacetyl tartaric acid.

Thus, the chiral tartaric acid may be di-p-anisolyl-D-tartaric acid, di-p-anisolyl-L-tartaric acid, D-diacetyl tartaric acid, or L-diacetyl tartaric acid. Preferably the L-isomer of di-p-anisolyl-tartaric acid or diacetyl tartaric acid is used. These resolving agents have the following structure (when R is $CH_3$, the resolving agent is diacetyl L-tartaric acid and R is MeO-Ph, the resolving agent is di-p-anisolyl-tartaric acid).

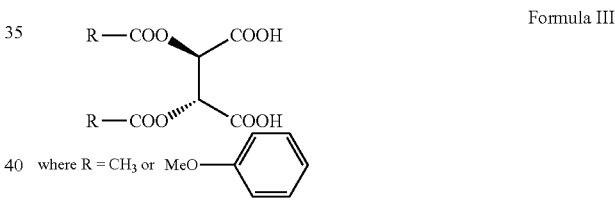

Formula III

In another embodiment, the solvent mixture used in the process of the present invention is a mixture of water with a polar aprotic solvent such as N,N-dimethyl formamide, dimethylsulfoxide, N,N-dimethylacetamide, sulfolane or N-methylpyrrolidone. Preferably, the solvent is a mixture of water and N-methylpyrrolidone.

In an embodiment, there is provided a salt of a chiral acid and eszopiclone obtained in the process of present invention, which salt is represented by Formula IV

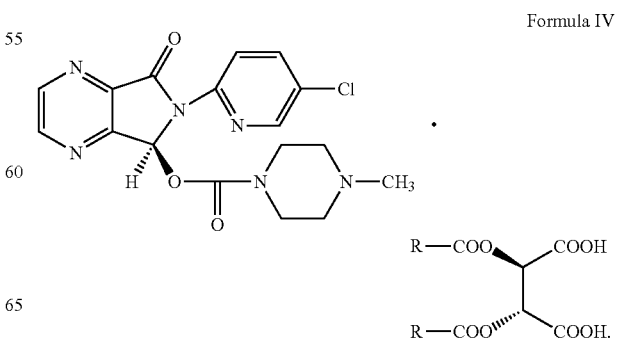

Formula IV where R = CH₃ or MeO— 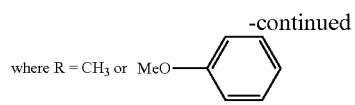

The racemic zopiclone of Formula II may be prepared by any known method.

The step a) of the process of present invention may be carried out at a temperature ranging from about 50° C. to about 70° C.

The term "eszopiclone substantially free of R-zopiclone" as used throughout this specification refers to an enantiomerically pure form of eszopiclone. In an embodiment, "eszopiclone substantially free of R-zopiclone" refers to eszopiclone having a chiral purity greater than or equal to 95%, preferably greater than 97%, more preferably greater than 99%.

In a further aspect of the present invention, the salt of eszopiclone and the resolving agent obtained in step a) is useful as an intermediate in the preparation of eszopiclone of Formula I.

The salts provided by the present invention such as eszopiclone di-p-anisolyl-L-tartaric acid or eszopiclone diacetyl-L-tartaric acid salt act as intermediates for the preparation of eszopiclone in step b).

The salt of step a) may be treated with a base which may be, for example, an organic base or an inorganic base to obtain eszopiclone. The organic base may be selected from pyridine, dimethylamine, trimethylamine and sodium ethoxide. The inorganic base may be selected from sodium carbonate, potassium carbonate, magnesium carbonate, calcium carbonate, sodium bicarbonate and potassium bicarbonate.

In an embodiment, the process of preparing eszopiclone according to the present invention comprises: (a) resolving racemic zopiclone with a resolving agent in the presence of a mixture of water and N-methylpyrrolidone to obtain the corresponding salt of eszopiclone and resolving agent; and (b) converting the salt prepared in step (a) to eszopiclone by treating the salt with a base. Advantageously, the eszopiclone is substantially free of R-zopiclone.

The resolution step (a) may be achieved by using a solvent mixture of water and N-methylpyrrolidone, and a resolving agent selected from the group consisting of di-p-anisolyl-L-tartaric acid, diacetyl-L-tartaric acid, O,O'-dibenzoyl tartaric acid monohydrate, D-malic acid, di-p-toluoyl-tartaric acid and tartaric acid.

The eszopiclone obtained by the process of the present invention may optionally be recrystallised using a solvent selected from ethanol, methanol, acetonitrile, acetone, ethyl acetate or propanol, most preferably ethyl acetate.

In an embodiment, the salt of the resolving agent and eszopiclone obtained by the process of the present invention has a chiral purity greater than or equal to 80%, preferably greater than or equal to 85%, more preferably greater than or equal to 90%.

In a preferred embodiment, the salt of the resolving agent and eszopiclone obtained by the process of the present invention has a chiral purity greater than or equal to 95%.

In a preferred embodiment, the eszopiclone obtained by the process of present invention has a chiral purity greater than or equal to 99%, as determined by chiral HPLC.

In still another aspect, the mother liquor which is enriched with the R-enantiomer is recycled by first racemizing it and then resolving using the process of the present invention.

The different polar aprotic solvents when used in combination with di-p-anisolyl-L-tartaric acid or diacetyl-L-tartaric acid resolving agents have a varied effect on the purity and yield of the corresponding chiral salt. The comparative results are shown in the Table below.

TABLE

| Resolving Agent | Solvent | Chiral Purity | Yield Of Salt |
|---|---|---|---|
| Di-p-anisolyl-L-tartaric acid | Water : NMP[1] | 97.70% | 95.89% |
| Diacetyl-L-tartaric acid | Water : NMP[1] | 95.61% | 95.14% |
| O,O'-dibenzoyl tartaric acid | Water : NMP[1] | 89.20% | 86.25% |
| Tartaric acid | Water : NMP[1] | 82.32% | 75.00% |
| Di-p-anisolyl-L-tartaric acid | Acetonitrile | 81.39% | 63.81% |
| Diacetyl-L-tartaric acid | Acetonitrile | 75.35% | 55.28% |
| O,O'-dibenzoyl tartaric acid | Acetonitrile | 56.00% | 22.17% |
| Tartaric acid | Acetonitrile | 49.56% | 19.78% |

[1]NMP = N-methylpyrrolidone

The present invention provides an improved process for resolving racemic zopiclone to obtain enantiomerically pure eszopiclone in high yield. The process is particularly advantageous in comparison with the known methods, as purity and yields are good. Also, the eszopiclone prepared from this process does not tend to racemise as seen in the prior art method. Further the solvent employed is a mixture with water which makes the process environmentally friendly. Another advantage of the process of present invention is that it is simple, practical, economical and an industrially-scalable technique.

EXAMPLES

The details of the invention are given in the examples which are provided below for illustration only and therefore these examples should not be construed to limit the scope of the invention.

Example 1

57 g of racemic zopiclone was added to a mixture of water and N-methylpyrrolidone. The reaction mixture was heated to 60-65° C. to obtain a clear solution. To this solution 63.8 g of di-p-anisolyl-L-tartaric acid was added and stirred at 60-65° C. for 1 hour. After completion of reaction, the mixture was cooled to 20-22° C. The resulting solid was filtered, washed with 3×250 ml of ethyl acetate and dried under vacuum to obtain eszopiclone di-p-anisolyl-L-tartaric acid salt (yield=97.70%, chiral purity=95.89%).

Example 2

75 g of zopiclone was added to a water and N-methylpyrrolidone mixture. On heating the reaction mixture to 60-65° C., a clear solution was obtained. To this solution 2.8 g of diacetyl-L-tartaric acid was added and stirred at 60-65° C. for 1 hour. After completion of reaction, the mixture was cooled to 20-22° C. The solid thus obtained was filtered, washed with 3×350 ml of ethyl acetate and dried under vacuum to obtain eszopiclone diacetyl-L-tartaric acid salt (yield=95.61%, chiral purity=95.14%).

Example 3

2.5 g of zopiclone was added to a mixture of water and N-methylpyrrolidone. The reaction mixture was heated to 60-65° C. to obtain a clear solution. To this solution 2.8 g of O,O'-dibenzoyl tartaric acid was added and stirred at 60-65° C. for 1 hour. After completion of reaction, the mixture was cooled to 20-22° C. The solid thus obtained was filtered, washed with 3×15 ml of ethyl acetate and dried under vacuum to obtain eszopiclone O,O'-dibenzoyl tartarate (yield=86.25%, chiral purity=89.20%).

Example 4

In a reaction vessel, a mixture of water and N,N-dimethylacetamide was taken and to it 2.5 g of racemic zopiclone was added. The reaction mixture was heated to 60-65° C. to obtain a clear solution. 2.8 g of di-p-anisolyl-L-tartaric acid was added to the solution and stirred at 60-65° C. for 1 hour. After completion of reaction, the mixture was cooled to 20-22° C. The resulting solid thus obtained was filtered, washed with 3×15 ml of ethyl acetate and dried under vacuum to yield eszopiclone di-p-anisolyl-L-tartaric acid salt (yield=55.41%, chiral purity=90.26%).

Example 5

In a reaction vessel, a mixture of water and N,N-dimethylsulfoxide was taken and to it 5 g of racemic zopiclone was added. The mixture was heated to 60-65° C. and a clear solution was obtained. To this solution 5.6 g of diacetyl-L-tartaric acid was added, and the solution was stirred at 60-65° C. for 1 hour. On completion of reaction the mixture was cooled to room temperature. The solid product thus obtained was filtered, washed with 3×25 ml of ethyl acetate and dried under vacuum to obtain eszopiclone diacetyl-L-tartaric acid salt (yield=44.71%, chiral purity=50%).

Example 6

Water and N-methylpyrrolidone mixture was added to 81.6 g of racemic zopiclone. The reaction mixture was heated to 60-65° C. to obtain a clear solution. To this solution 92.1 g of di-p-toluoyl-L-tartaric acid was added and the solution was stirred at 60-65° C. for 1 hour. After completion of reaction, the mixture was cooled at 20-22° C. The resulting solid was filtered, washed with 3×300 ml of ethyl acetate and dried under vacuum to obtain eszopiclone di-p-toluoyl-L-tartaric acid salt (yield=81.50%, chiral purity=87.30%).

Example 7

55 g of eszopiclone di-p-anisolyl-L-tartarate salt, obtained from Example 1, was added to a mixture of 600 ml dichloromethane and 300 ml of water. The contents was cooled to 10° C. and the pH was adjusted to 8-9 by adding 10% sodium carbonate solution. The organic layer was separated and aqueous layer was extracted with 250 ml dichloromethane. The combined organic layer was washed with 1×500 ml water. The organic layer was dried over sodium sulphate and concentrated under vacuum at 40-45° C. The concentrated organic layer was stripped with 4×150 ml ethyl acetate and concentrated until dry to obtain a solid. This solid was further dissolved in ethyl acetate at 70-77° C. and gradually cooled to 22-23° C. The resulting solution was stirred for 2 hours, filtered and washed with ethyl acetate (1×350 ml). The solid was dried under vacuum at 70-75° C. for about 20-24 hours to obtain 17.5 g of eszopiclone (chiral purity=99.8%).

Example 8

75 g of eszopiclone diacetyl-L-tartaric acid salt, obtained from Example 2, was added to a mixture of 700 ml dichloromethane and 350 ml of water. The contents was cooled to 10° C. and the pH was adjusted to 8-9 by adding 10% sodium carbonate solution. The organic layer was separated and the aqueous layer was extracted with 400 ml dichloromethane. The combined organic layer was washed with 1×750 ml water. The organic layer was dried over sodium sulphate and concentrated under vacuum at 40-45° C. The concentrated organic layer was stripped with 4×175 ml ethyl acetate and concentrated until dry to obtain a solid. This solid was dissolved in ethyl acetate at 70-77° C. and gradually cooled to 22-23° C. The resulting solution was stirred for 2 hours, filtered and washed with ethyl acetate (1×500 ml). The solid was dried under vacuum at 70-75° C. for about 20-24 hrs to obtain 21 g of eszopiclone (chiral purity=above 99.3%).

It will be appreciated that the invention may be modified within the scope of the appended claims.

The invention claimed is:

1. A process for preparing the di-p-anisolyl-L-tartrate or diacetyl L-tartrate salt of eszopiclone, which process comprises reacting racemic zopiclone with di-p-anisolyl-L-tartaric acid or diacetyl L-tartaric acid, respectively, wherein the process is carried out in the presence of a solvent mixture and wherein the solvent mixture is a mixture of water and N-methylpyrrolidone.

2. The process according to claim 1, wherein the salt of eszopiclone has a chiral purity greater than or equal to 95%.

3. A process for preparing eszopiclone comprising preparing a salt of eszopiclone according to claim 1, and reacting the salt of eszopiclone with a base.

4. The process according to claim 3, wherein the base is selected from the group consisting of pyridine, dimethylamine, trimethylamine, sodium ethoxide, sodium carbonate, potassium carbonate, magnesium carbonate, calcium carbonate, sodium bicarbonate and potassium bicarbonate.

5. The process according to claim 3, wherein the eszopiclone is recrystallised using a solvent selected from ethanol, methanol, acetonitrile, acetone, ethyl acetate or propanol.

6. The process according to claim 5, wherein the solvent is ethyl acetate.

7. The process according to claim 5, wherein the eszopiclone has a chiral purity greater than or equal to 99%.

8. The process according to claim 3, wherein the salt of eszopiclone has a chiral purity greater than or equal to 95%.

9. The process according to claim 4, wherein the eszopiclone is recrystallised using a solvent selected from ethanol, methanol, acetonitrile, acetone, ethyl acetate or propanol.

10. The process according to claim 6, wherein the eszopiclone has a chiral purity greater than or equal to 99%.

* * * * *